United States Patent [19]

Minai et al.

[11] Patent Number: 4,496,767

[45] Date of Patent: Jan. 29, 1985

[54] PROCESS FOR PREPARING 2-CYCLOPENTENONE DERIVATIVES

[75] Inventors: Masayoshi Minai, Moriyama; Tadashi Katsura, Suita, both of Japan

[73] Assignee: Sumitomo Chemical Company, Limited, Osaka, Japan

[21] Appl. No.: 543,152

[22] Filed: Oct. 18, 1983

[30] Foreign Application Priority Data

Oct. 27, 1982 [JP] Japan .............................. 57-189883

[51] Int. Cl.³ ............................................. C07C 45/65
[52] U.S. Cl. .................................... 568/346; 568/361; 568/314; 568/322; 560/254; 560/255; 560/231
[58] Field of Search ....................... 560/254, 255, 231; 568/346, 361, 314, 322

[56] References Cited

U.S. PATENT DOCUMENTS 3,947,519  3/1976  Matsui et al. ........................ 568/346
4,132,726  1/1979  Kurozumi et al. .................. 560/231
4,398,043  8/1983  Saito et al. .......................... 568/322

OTHER PUBLICATIONS

Scettri et al., Tetrahedron, vol. 35, pp. 135–138, (1979).
Piancatelli et al., Tetrahedron Letters, #37, pp. 3555–3558, (1976).

Primary Examiner—James H. Reamer
Attorney, Agent, or Firm—Birch, Stewart, Kolasch & Birch

[57] ABSTRACT

A novel process for preparing 2-cyclopentenones of the formula:

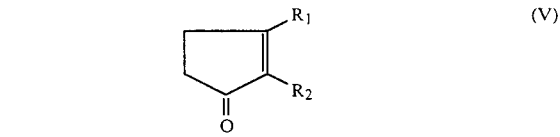

wherein $R_1$ is hydrogen, alkyl or alkenyl and $R_2$ is alkyl, alkenyl, alkynyl, cycloalkyl, aryl or aralkyl, which comprises esterifying a mixture of a 3-hydroxy-4-cyclopentenone of the formula:

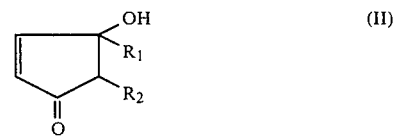

wherein $R_1$ and $R_2$ are each as defined above and a 4-hydroxy-2-cyclopentenone of the formulas:

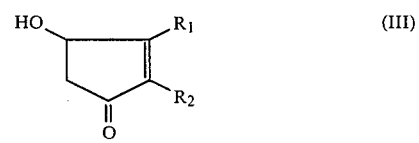

wherein $R_1$ and $R_2$ are each as defined above with an aliphatic carboxylic acid to give a mixture of the 4-hydroxy-2-cyclopentenone (III) and the cyclopentenone ester of the formula:

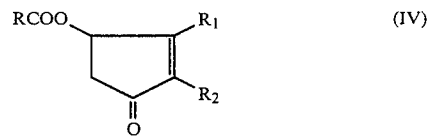

wherein $R_1$ and $R_2$ are each as defined above and R is hydrogen or $C_1$–$C_4$ alkyl and subjecting the resulting mixture to reduction.

13 Claims, No Drawings

PROCESS FOR PREPARING 2-CYCLOPENTENONE DERIVATIVES

The present invention relates to a process for preparing 2-cyclopentenone derivatives. More particularly, it relates to a novel process for preparing 2-cyclopentenones of the formula:

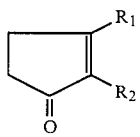
(V)

wherein $R_1$ is hydrogen, alkyl (e.g. methyl, ethyl, propyl, butyl, pentyl, hexyl, heptyl, octyl) or alkenyl (e.g. allyl, methallyl, 2-pentenyl) and $R_2$ is alkyl (e.g. methyl, ethyl, propyl, butyl, pentyl, hexyl, heptyl, octyl), alkenyl (e.g. allyl, methallyl, 2-pentenyl), alkynyl (e.g. propargyl), cycloalkyl (e.g. cyclopentyl, cyclohexyl), aryl (e.g. phenyl, tolyl, naphthyl, alpha-methylphenyl) or aralkyl (e.g. benzyl, phenethyl).

The atomic groups as above mentioned usually have not more than 16 carbon atoms. Particularly when the atomic group is alkyl, alkenyl, alkynyl or cycloalkyl, it is preferred to have not more than 8 carbon atoms.

The 2-cyclopentenones (V) have various practical uses. For instance, they are useful as perfumes such as jasmone. They are also useful as intermediates in the synthesis of chemical substances to be used as perfumes.

According to the present invention, there is provided a process for preparing the 2-cyclopentenone derivatives (V) in an industrially advantageous manner with a low cost.

There are hitherto known some procedures for preparing the 2-cyclopentenone derivatives (V), of which typical examples are shown in the following scheme:

Procedure 1
Japanese Patent Publn. (unexamined) NO. 46833/1981

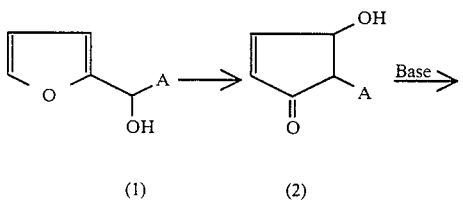

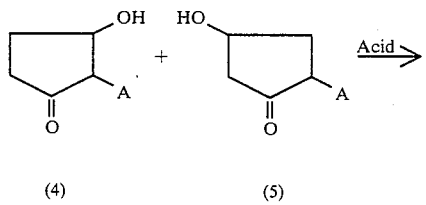

Procedure 2
Japanese Patent Publn. (unexamined) No. 72934/1982

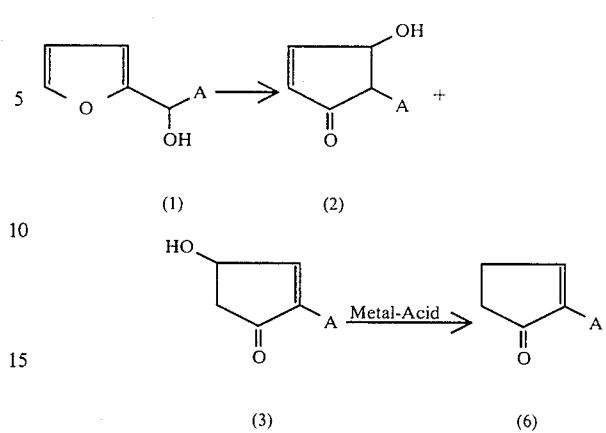

Procedure 3
Japanese Patent Publn. (unexamined) No. 95935/1982

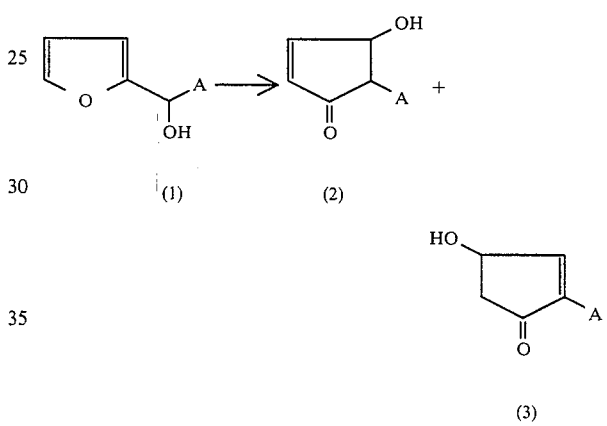

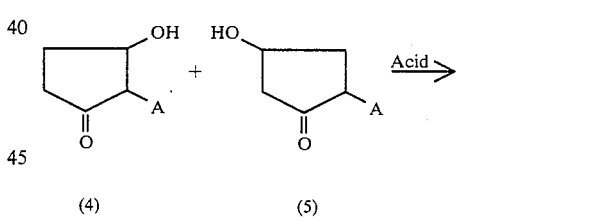

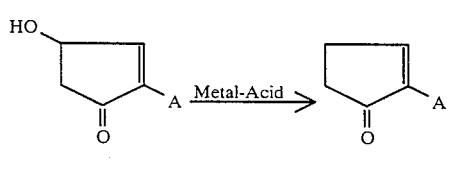

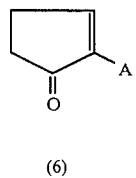

Among them, Procedure 1 comprises the step of rearrangement of the compound (2) to the compound (3) under a basic condition, followed by the step of reduction. The isolation of the compound (2) and of the compound (3) is needed for obtaining the objective compound (6) with a high purity. This is inconvenient from the industrial viewpoint.

In Procedure 2, a mixture of the compounds (2) and (3) is reduced with a metal and an acid to give the objective compound (6). Since the starting material contains the compound (2), the contamination of the compound (6) with a cyclopentanone is unavoidable. For separation and purification of the desired compound (6), a troublesome operation is needed. Further, the metal is blocked in the reduction step, and a problem in operation arises therefrom.

In Procedure 3, a mixture of the compounds (2) and (3) is reduced to give a mixture of the compounds (4) and (5), which is then dehydrated to give the objective compound (6). Separation of the compounds (2) and (3) and of the compounds (4) and (5) is required for obtaining the objective compound (6) in a high purity. This is inconvenient from the industrial viewpoint.

As a result of an extensive study, it has now been found that the 2-cyclopentanone derivative (V) can be prepared advantageously from a furan-carbinol of the formula:

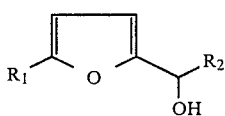
(I)

wherein $R_1$ and $R_2$ are each as defined above through a 3-hydroxy-4-cyclopentenone of the formula:

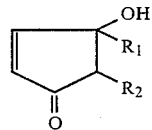
(II)

wherein $R_1$ and $R_2$ are each as defined above in a high yield and a high purity without any drawback as seen in the conventional procedures.

According to the present invention, the furan-carbinol (I) is rearranged to give a mixture of the 3-hydroxy-4-cyclopentenone (II) and a 4-hydroxy-2-cyclopentenone of the formula:

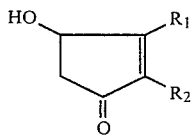
(III)

wherein $R_1$ and $R_2$ are each as defined above, esterifying this mixture with an aliphatic carboxylic acid to give a mixture of a cyclopentanone ester of the formula:

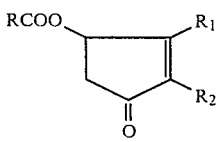
(IV)

wherein $R_1$ and $R_2$ are each as defined above and R is hydrogen or $C_1$-$C_4$ alkyl and the 3-hydroxy-2-cyclopentenone (III), and subjecting this mixture to reduction.

The starting furan-carbinol (I) may be prepared by any conventional procedure, of which typical examples are shown in the following scheme:

Procedure A

Reaction of the corresponding 5-substituted furfural with a Grignard reagent:

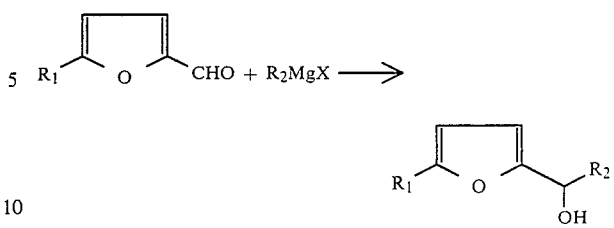

wherein $R_1$ and $R_2$ are each as defined above and X is a halogen atom.

Procedure B

Reaction of the corresponding 2-substituted furan with an aldehyde in the presence of a basic catalyst:

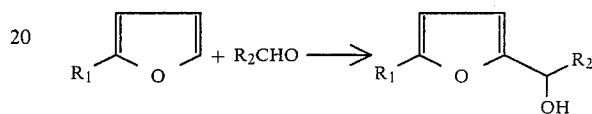

wherein $R_1$ and $R_2$ are each as defined above and X is halogen.

Examples of the furan-carbinol (I) are as follows: α-methylfurfuryl alcohol, α-ethylfurfuryl alcohol, α-n-propylfurfuryl alcohol, α-isopropylfurfuryl alcohol, α-n-butylfurfuryl alcohol, α-isobutylfurfuryl alcohol, α-n-pentylfurfuryl alcohol, α-isopentylfurfuryl alcohol, α-n-hexylfurfuryl alcohol, α-n-heptylfurfuryl alcohol, α-allylfurfuryl alcohol, α-(2-cis-butenyl)furfuryl alcohol, α-ω-butenylfurfuryl alcohol, α-(2-cis-pentenyl)furfuryl alcohol, α-(2-trans-pentenyl)furfuryl alcohol, α-(3-cis-hexenyl)furfuryl alcohol, α-propargylfurfuryl alcohol, α-(2-pentynyl)furfuryl alcohol, α-cyclopentylfurfuryl alcohol, α-cyclohexylfurfuryl alcohol, α-cycloheptylfurfuryl alcohol, α-phenylfurfuryl alcohol, α-benzylfurfuryl alcohol, 5-methyl-α-methylfurfuryl alcohol, 5-methyl-α-ethylfurfuryl alcohol, 5-methyl-α-n-propylfurfuryl alcohol, 5-methyl-α-isopropylfurfuryl alcohol, 5-methyl-α-n-butylfurfuryl alcohol, 5-methyl-α-isobutylfurfuryl alcohol, 5-methyl-α-n-pentylfurfuryl alcohol, 5-methyl-α-isopentylfurfuryl alcohol, 5-methyl-α-n-hexylfurfuryl alcohol, 5-methyl-α-n-heptylfurfuryl alcohol, 5-methyl-α-allylfurfuryl alcohol, 5-methyl-α-(2-cis-butenyl)furfuryl alcohol, 5-methyl-α-(ω-butenyl)furfuryl alcohol, 5-methyl-α-(2-cis-pentenyl)-furfuryl alcohol, 5-methyl-α-(2-trans-pentenyl)furfuryl alcohol, 5-methyl-α-(3-cis-hexenyl)furfuryl alcohol, 5-methyl-α-propargylfurfuryl alcohol, 5-methyl-α-(2-pentynyl)furfuryl alcohol, 5-methyl-α-cyclopentylfurfuryl alcohol, 5-methyl-α-cyclohexylfurfuryl alcohol, 5-methyl-α-cycloheptylfurfuryl alcohol, 5-methyl-α-phenylfurfuryl alcohol, 5-methyl-α-benzylfurfuryl alcohol, etc.

The aqueous medium wherein the rearrangement is carried out may comprise water or water admixed with a small amount of any organic solvent. As the organic solvent, there may be employed any one inert to the rearrangement chosen from aliphatic or aromatic hydrocarbons, halogenated hydrocarbons, alcohols, carboxylic acids, ethers, esters, etc. Specific examples are ethylene glycol, 1,3-propanediol, methanol, ethanol, dioxane, tetrahydrofuran, dimethylformamide, dimethylsulfoxide, ethyl acetate, acetic acid, dichloromethane, toluene, dimethyl ether, etc. The sole use of water is usually preferred from the economical reason.

For the rearrangement, the use of a catalyst is not essential. However, its use is favorable for enhancement of the reaction rate and increase of the conversion. As the catalyst, there may be used any suitable one chosen from metal salts, organic quaternary ammonium salts, surfactants, alcohols, etc. Examples of the metal salts are phosphates, sulfates, chlorides, bromides, oxides, carboxylates, sulfonates, etc. of sodium, potassium, magnesium, zinc, iron, calcium, manganese, cobalt, aluminum, etc. Examples of the organic quaternary ammonium salts are tetrabutylammonium bromide, benzyltrimethylammonium chloride, tricaprylmethylammonium chloride, dodecyltrimethylammonium chloride, caprylbenzyldimethylammonium chloride, etc. Examples of the surfactants are higher fatty acid salts, polyoxyethylene alkylphenol ethers, higher fatty alcohols, etc. Examples of the alcohols are methanol, ethanol, ethylene glycol, etc. These may be used alone or in combination. Further, the alcohols may play the roles of the reaction medium and the catalyst simultaneously. The amount of the catalyst is not limitative and may be usually from 1/200 to 5 times of the weight of the furancarbinol (I).

The reaction system may be kept at any pH and is normally within a pH range of 3 to 7, particularly of 3.5 to 6.5. For maintenance of such pH range, organic or inoganic acidic or basic substances may be employed. Specific examples of the acidic substances are hydrochloric acid, sulfuric acid, phosphoric acid, boric acid, acetic acid, propionic acid, toluenesulfonic acid, methanesulfonic acid, etc. Specific examples of the basic substances are sodium hydroxide, potassium carbonate, sodium hydrogen carbonate, potassium monohydrogen phosphate, triethylamine, dimethylaniline, etc. Any buffer obtainable by the combination of an acidic substance and a basic substance is also usable, and examples of such combination are potassium monohydrogen phosphate/phosphoric acid, sodium acetate/acetic acid, sodium acetate/phosphoric acid, phthalic acid/potassium carbonate, potassium monohydrogen phosphate/hydrochloric acid, potassium dihydrogen phosphate/potassium hydrogen carbonate, succinic acid/sodium hydrogen carbonate, etc. In general, however, the use of a strong acid (e.g. hydrochloric acid, hydrobromic acid) or a strong alkali (e.g. sodium hydroxide, potassium hydroxide) is not favorable.

The rearrangement takes place usually at a temperature between 0° and 200° C., preferably between 20 and 160° C.

From the reaction mixture, a mixture of the 3-hydroxy-4-cyclopentenone (II) and the 4-hydroxy-2-cyclopentenone (III) as the rearranged product can be readily recovered in a high yield by application of a conventional separation procedure such as extraction, fractionation, concentration or disillation.

The subsequent esterification of the mixture of the 3-hydroxy-4-cyclopentenone (II) and the 4-hydroxy-2-cyclopentenone (III) as above obtained with an aliphatic carboxylic acid may be carried out by heating them in the presence or absence of any inert solvent.

As the aliphatic carboxylic acid, there may be normally employed the one having not more than 5 carbon atoms such as formic acid, acetic acid, propionic acid, butyric acid or valeric acid. These may be used alone or in combination. Further, these acids may be used in combination with their metal salts or organic amine salts. As the metal salts, there are exemplified lithium salt, sodium salt, potassium salt, calcium salt, copper salt, zinc salt, palladium salt, lead salt, tin salt, manganese salt, cobalt salt, etc. Examples of the organic amine salts are triethylamine salt, pyridine salt, picoline salt, trimethylamine salt, etc.

The aliphatic carboxylic acid is usually employed in not less than one equivalent amount, preferably not less than two equivalent amount, to the 3-hydroxy-4-cyclopentenone (II).

As the inert solvent, there may be used any one chosen from aliphatic or aromatic hydrocarbons, halogenated hydrocarbons, ethers, etc. Specific examples are tetrahydrofuran, diethyl ether, acetone, methylethylketone, toluene, benzene, chlorobenzene, dichloromethane, dichloroethane, chloroform, carbon tetrachloride, dimethylformamide, dimethylsulfoxide, hexane, etc. Any aliphatic carboxylic acid is also usable as the solvent.

The reaction is ordinarily effected at a temperature of 0° to 150° C., preferably of 30° to 140° C.

As the result of the above reaction, the 3-hydroxy-4-cyclopentenone (II) is readily converted into the cyclopentenone ester (IV), and a mixture of the cyclopentenone ester (IV) and the 4-hydroxy-2-cyclopentenone (III) is thus obtained as the reaction product.

The reduction of the mixture of the cyclopentenone ester (IV) and the 4-hydroxy-2-cyclopentenone (III) as above obtained to the 2-cyclopentenone (V) is normally carried out by treatment with a metal and an acid. Since the reaction mixture in the preceding step usually contains the aliphatic carboxylic acid, such aliphatic carboxylic acid itself may be used as the acid required for the reduction. When necessary or desired, however, any acid may be incorporated into the said reaction mixture. Examples of the acid are formic acid, acetic acid, propionic acid, butyric acid, valeric acid, hydrochloric acid, sulfuric acid, phosphoric acid, chloric acid, etc. Any substance which produces an acid in the reaction with water may also be used, and examples thereof are acid anhydrides (e.g. acetic anhydride, propionic anhydride). The amount of the acid is not limitative and may be usually from 1 to 30 times of the weight of the mixture of the cyclopentenone ester (IV) and the 4-hydroxy-2-cyclopentenone (III) as the starting material in this step.

As the metal, there may be used any one which is conventionally employed for the reduction reaction. Specific examples are zinc, amalgamated zinc, iron, tin, etc. The amount of the metal may be from 0.5 to 50 mol per one mol of the starting mixture.

Application of any conventional separation procedure such as filtration, concentration, extraction, fractionation or distillation to the reaction mixture from the reduction step can afford the 2-cyclopentenone (V) in a good yield.

Practical and presently preferred embodiments of the invention are illustratively shown in the following Examples, wherein part(s) are by weight unless otherwise indicated.

EXAMPLE 1

In a four-necked flask equipped with a stirrer and a thermometer, there were charged 5-methyl-α-allylfurfuryl alcohol (I-1) (152 g), water (4560 g) and a buffer solution (5.1 g) comprising potassium monohydrogen phosphate/phosphoric acid adjusted to pH 4.8, and the mixture was stirred at 100° C. for 15 hours under a nitrogen stream. After completion of the reaction, the reaction mixture was cooled and extracted twice with methyl isobutyl ketone (600 ml). Removal of methyl isobutyl ketone from the extract gave a mixture (132.2 g) of 2-allyl-3-hydroxy-3-methyl-4-cyclopentenone (II-1) and 2-allyl-4-hydroxy-3-methyl-2-cyclopentenone (III-1). Yield, 87%.

To the mixture (120 g), sodium acetate (18 g) and acetic acid (480 g) were added, and the resultant mixture was heated at 110°-120° C. for 4 hours. The reaction mixture was analyzed by gas chromatography and confirmed not to contain 2-allyl-3-hydroxy-3-methyl-4-cyclopentenone (II-1).

The reaction mixture was cooled to 60° C., zinc powder (200 g) was added thereto and the resultant mixture was further heated at 110°-120° C. for 4 hours. After completion of the reaction, insoluble materials were collected by filtration, and the filtrate was concentrated under reduced pressure. To the concentrated residue, there were added hexane (200 ml) and water (100 ml). The organic layer was separated and washed with a 3% aqueous sodium bicarbonate solution and water in order, and dried over magnesium sulfate and concentrated to give 101.48 g of 2-allyl-3-methyl-2-cyclopentenone (V-1). Yield, 94.6% (based on the combined amount of the compounds (II-1) and (III-1)). B.P., 66°-70° C./2-3 mmHg.

2-Allyl-3-methylcyclopentanone was by-produced in a yield of 0.15%.

EXAMPLE 2

In the same flask as used in Example 1, there were charged 5-methyl-α-(2-cis-pentenyl)furfuryl alcohol (I-2) (18 g) and water (720 g), and the mixture was stirred at 100° C. under a pH of 4.7-4.9. The reaction mixture was then treated in the same manner as in Example 1 to give a mixture (14.2 g) of 2-(2-cis-pentenyl)-3-hydroxy-3-methyl-4-cyclopentenone (II-2) and 2-(2-cis-pentenyl)-4-hydroxy-3-methyl-2-cyclopentenone (III-2). Yield, 79%.

To the mixture (12 g), sodium acetate (2 g) and acetic acid (50 g) were added, and the resultant mixture was heated at 110° C. for 4 hours.

The inner temperature of the reaction mixture was cooled to 60° C., zinc powder (24 g) was added thereto and the resultant mixture was further heated at 90°-100° C. for 4 hours. After completion of the reaction, the same post-treatment as in Example 1 was effected to give 10.45 g of 2-(2-cis-pentenyl)-3-methyl-2-cyclopentenone (V-2). Yield, 95.5% (based on the combined amount of the compounds (II-2) and (III-2)). B.P., 100°-105° C./4-5 mmHg.

2-(2-cis-Pentenyl)-3-methylcyclopentanone was by-produced in a yield of 0.1%.

EXAMPLE 3

In the same flask as used in Example 1, there were charged α-n-pentylfurfuryl alcohol (I-3) (33.6 g) and water (1680 g), and the mixture was stirred at 100° C. while adjusting to a pH of 4.6-5.0. The reaction mixture was treated in the same manner as in Example 1 to give a mixture (29.2 g) of 2-n-pentyl-3-hydroxy-4-cyclopentenone (II-3) and 2-n-pentyl-4-hydroxy-2-cyclopentenone (III-3). Yield, 87%.

The mixture (14 g) was dissolved in acetic acid (50 g), sodium acetate (2.5 g) was added thereto, and the resulting mixture was heated at 80°-90° C. for 6 hours.

Then, zinc powder (21 g) was added thereto, and the resultant mixture was heated at 80°-100° C. for 4 hours. After completion of the reaction, the same post-treatment as in Example 1 was effected to give 12.12 g of 2-n-pentyl-2-cyclopentenone (V-3). Yield, 95.7% (based on the combined amount of the compounds (II-3) and (III-3)). B.P., 80°-90° C./3-5 mmHg.

2-n-Pentylcyclopentanone was by-produced in a yield of 0.3%.

EXAMPLE 4

In an autoclave, there were charged α-n-hexylfurfuryl alcohol (I-4) (18.2 g), water (910 g) and a buffer solution (0.6 g) comprising sodium acetate and acetic acid adjusted to pH 4.7. The resultant mixture was stirred at 110° C. under a nitrogen stream. After completion of the reaction, the reaction mixture was cooled and extracted with toluene. Removal of toluene from the extract gave a mixture (15.65 g) of 2-n-hexyl-3-hydroxy-4-cyclopentenone (II-4) and 2-n-hexyl-4-hydroxy-2-cyclopentenone (III-4). Yield, 86%.

The mixture (14 g) was dissolved in acetic acid (56 g), and copper acetate (2.8 g) was added thereto. The mixture was then heated at 80°-100° C. for 4 hours.

After being allowed to cool, tin (30 g) was added thereto, and the resultant mixture was further stirred at 80°-100° C. for 4 hours. After completion of the reaction, the same post-treatment as in Example 1 was effected to give 12.12 g of 2-n-hexyl-2-cyclopentenone (V-4). Yield, 94.9% (based on the combined amount of the compounds (II-4) and (III-4)). B.P., 95°-98° C./4-5 mmHg.

2-n-Hexylcyclopentanone was by-produced in a yield of 0.28%.

EXAMPLES 5 TO 13

In the same manner as above, the rearrangement of the furan-carbinol (I) to a mixture of the 3-hydroxy-4-cyclopentenone (II) and the 4-hydroxy-2-cyclopentenone (III), the esterification of the mixture of the 3-hydroxy-4-cyclopentenone (II) and the 4-hydroxy-2-cyclopentenone (III) to a mixture of the cyclopentenone ester (IV) and the 4-hydroxy-2-cyclopentenone (III) and the reduction of the mixture of the cyclopentenone ester (IV) and the 4-hydroxy-2-cyclopentenone (III) to the 2-cyclopentenone (V) were carried out. The results are shown in Table 1 (rearrangement), Table 2 (esterification) and Table 3 (reduction).

The amounts of the catalyst and the solvent in Table 1, the amounts of the aliphatic carboxylic acid and the solvent in Table 2 and the amounts of metal and the acid in Table 3 are indicated in part(s) to one part of the starting material. The yield in Table 1 shows the total yield of the 3-hydroxy-4-cyclopentenone (II) and the 4-hydroxy-2-cyclopentenone (III). The starting material in Table 3 (not shown) is the reaction product, i.e. the mixture of the 4-hydroxy-2-cyclopentenone (III) and the cyclopentenone ester (IV), in Table 2.

TABLE 1

| | Furan-carbinol (I) | | (Rearrangement) Catalyst | | Solvent | | | Reaction | Yield |
|---|---|---|---|---|---|---|---|---|---|
| Example No. | R₁ | R₂ | Material | Amount (part) | Material | Amount (part) | pH | temp. (°C.) | (%) |
| 5 | CH₃ | n-C₅H₁₁ | Sodium acetate/ acetic acid | 1/30 | Water Ethylene glycol | 40 1 | 4.8–5.0 | 100 | 78 |
| 6 | H | CH₂C≡CH | — | — | Water | 30 | 4.6–4.9 | 100 | 81 |
| 7 | CH₃ | trans CH₂CH=CHC₂H₅ | Tetrabutyl-ammonium bromide | 1/50 | Water | 40 | 5.0–5.2 | 100 | 75 |
| 8 | H | ⟨H⟩ | Sodium acetate/ phosphoric acid | 1/50 | Water | 30 | 5.2 | 110 | 74 |
| 9 | CH₃ | CH₂C≡CH | Potassium mono-hydrogen phosphate/phosphoric acid | 1/30 | Water | 30 | 4.7–5.1 | 100 | 81 |
| 10 | CH₃ | ⟨phenyl⟩ | Emulgen 910*¹ | 1/30 | Water | 30 | 4.7–5.4 | 100 | 70 |
| 11 | CH₃ | n-C₃H₇ | — | — | Water | 30 | 4.8–5.3 | 120 | 67 |
| 12 | H | cis CH₂CH=CHC₂H₅ | Sodium acetate Phosphoric acid/ magnesium chloride | 1/50 1/30 | Water | 40 | 4.9–5.1 | 100 | 76 |
| 13 | CH₃ | CH₂CH=CH₂ | — | — | Water | 30 | 4.7–5.1 | 100 | 81 |

Note:
*¹Polyoxyethylene nonylphenyl ether; manufactured by Kao Atlas Co.

TABLE 2

| | 3-Hydroxy-4-cyclopentenone (II) + 4-Hydroxy-2-cyclopentenone (III) | | (Esterification) Aliphatic carboxylic acid | | Solvent | | Reaction temp. | Reaction time |
|---|---|---|---|---|---|---|---|---|
| Example No. | R₁ | R₂ | Material | Amount (part) | Material | Amount (part) | (°C.) | (hr) |
| 5 | CH₃ | n-C₅H₁₁ | Acetic acid | 5 | — | — | 110 | 4 |
| 6 | H | CH₂C≡CH | Acetic acid Sodium acetate | 4 1/5 | — | — | 90–100 | 4 |
| 7 | CH₃ | trans CH₂=CHC₂H₅ | Acetic acid Sodium acetate | 4 ¼ | — | — | 90–100 | 4 |
| 8 | H | ⟨H⟩ | Acetic acid Sodium acetate | 3 1/5 | — | — | 90–100 | 3 |
| 9 | CH₃ | CH₂C≡CH | Acetic acid Sodium acetate | 4 1/5 | — | — | 80–100 | 4 |
| 10 | CH₃ | ⟨phenyl⟩ | Acetic acid Copper acetate | 3 ¼ | — | — | 100 | 3 |
| 11 | CH₃ | n-C₃H₇ | Acetic acid Copper acetate | 3 ¼ | Toluene | 1 | 100–110 | 4 |
| 12 | H | cis CH₂CH=CHC₂H₅ | Acetic acid Sodium acetate | 4 1/5 | — | — | 100–110 | 3 |
| 13 | CH₃ | CH₂CH=CH₂ | Propionic acid Sodium propionate | 4 1/5 | — | — | 100–110 | 4 |

TABLE 3

| | Metal | | Acid | | Reaction temp. | Reaction time | 2-Cyclopentenone (V) | | Yield (By-production of cyclopentanone; %) |
|---|---|---|---|---|---|---|---|---|---|
| Example No. | Material | Amount (part) | Material | Amount (part) | (°C.) | (hr) | R₁ | R₂ | |
| 5 | Zinc | 1.5 | — | — | 100–110 | 3 | CH₃ | n-C₅H₁₁ | 92.9 (0.06) |

TABLE 3-continued

| | | | | (Reduction) | | | | |
|---|---|---|---|---|---|---|---|---|
| | Metal | | Acid | | Reaction temp. (°C.) | Reaction time (hr) | 2-Cyclopentenone (V) | |
| Example No. | Material | Amount (part) | Material | Amount (part) | | | $R_1$ $R_2$ | Yield (By-production of cyclopentanone; %) |
| 6 | Zinc | 3 | — | — | 100–110 | 3 | H  $CH_2CH=CH_2$ | 94.8 (0.35) |
| 7 | Zinc | 2 | — | — | 90–100 | 3 | $CH_3$  trans $CH_2CH=CHC_2H_5$ | 94.3 (0.09) |
| 8 | Zinc | 2 | Acetic anhydride | 1/4 | 80–90 | 2 | H  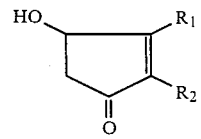 | 93.8 (0.35) |
| 9 | Zinc | 3 | — | — | 90–100 | 3 | $CH_3$  $CH_2CH=CH_2$ | 92.2 (0.14) |
| 10 | Tin | 3 | Acetic acid | 1 | 80–100 | 4 | $CH_3$  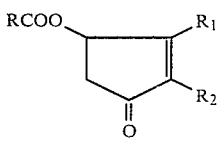 | 92.1 (0.1) |
| 11 | Zinc | 2 | — | — | 100–110 | 4 | $CH_3$  n-$C_3H_7$ | 95.2 (0.11) |
| 12 | Zinc | 1.5 | Acetic anhydride | 1/5 | 100 | 3 | H  cis $CH_2CH=CHC_2H_5$ | 93.8 (0.24) |
| 13 | Zinc | 1.5 | — | — | 80–100 | 4 | $CH_3$  $CH_2CH=CH_2$ | 94.4 (0.08) |

COMPARATIVE EXAMPLE 1

A mixture (14 g) of 2-n-pentyl-3-hydroxy-4-cyclopentenone (II-3) and 2-n-pentyl-4-hydroxy-2-cyclopentenone (III-3) obtained in Example 3 was dissolved in acetic acid (80 g), zinc powder (17 g) was added thereto, and the resultant mixture was stirred at 80°–90° C. for 0.5 hour. After completion of the reaction, the reaction mixture was cooled, the precipitants were collected by filtration and the filtrate was extracted with toluene. The extract was washed with aqueous alkali and then water. The toluene layer was concentrated by distillation to give 11.65 g of 2-n-pentyl-2-cyclopentenone. Yield, 92%.

2-n-Pentylcyclopentanone was by-produced in a yield of 4.1%.

What is claimed is:

1. A process for preparing 2-cyclopentenones of the formula:

(V)

wherein $R_1$ is hydrogen, alkyl or alkenyl and $R_2$ is alkyl, alkenyl, alkynyl, cycloalkyl, aryl or aralkyl, which comprises esterifying a mixture of a 3-hydroxy-4-cyclopentenone of the formula:

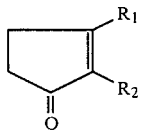

(II)

wherein $R_1$ and $R_2$ are each as defined above and a 4-hydroxy-2-cyclopentenone of the formula:

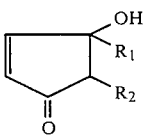

(III)

wherein $R_1$ and $R_2$ are each as defined above with an aliphatic carboxylic acid to give a mixture of the 4-hydroxy-2-cyclopentenone (III) and a cyclopentenone ester of the formula:

(IV)

wherein $R_1$ and $R_2$ are each as defined above and R is hydrogen or $C_1$–$C_4$ alkyl and subjecting the resulting mixture to reduction.

2. The process according to claim 1, wherein the mixture of the 3-hydroxy-4-cyclopentenone (II) and the 4-hydroxy-2-cyclopentenone (III) is obtained by rearrangement of a furan-carbinol of the formula:

(I)

wherein $R_1$ is hydrogen, alkyl or alkenyl and $R_2$ are alkyl, alkenyl, alkynyl, cycloalkyl, aryl or aralkyl in an aqueous medium in the presence or absence of a catalyst.

3. The process according to claim 1, wherein the aliphatic carboxylic acid in the esterification is a carboxylic acid having not more than 5 carbon atoms.

4. The process according to claim 3, wherein the aliphatic carboxylic acid is chosen from formic acid, acetic acid, propionic acid, butyric acid and valeric acid.

5. The process according to claim 1, wherein the aliphatic carboxylic acid in the esterification is used in combination with at least one of the metal salts and organic amine salts thereof.

6. The process according to claim 5, wherein the metal salt or organic amine salt is chosen from the lithium salt, sodium salt, potassium salt, calcium salt, copper salt, zinc salt, palladium salt, lead salt, tin salt, manganese salt, cobalt salt, triethylamine salt, pyridine salt, picoline salt and trimethylamine salt.

7. The process according to claim 1, wherein the aliphatic carboxylic acid in the esterification is employed in an amount which is not less than one quivalent with respect to the amount of 3-hydroxy-4-cyclopentenone.

8. The process according to claim 1, wherein the the esterification is carried out at a temperature of 0° to 150° C.

9. The process according to claim 1, wherein the reduction is carried out with a metal and an acid.

10. The process according to claim 9, wherein the metal is chosen from zinc, amalgamated zinc, iron and tin.

11. The process according to claim 9, wherein the acid is chosen from formic acid, acetic acid, propionic acid, butyric acid, valeric acid, hydrochloric acid, sulfuric acid, phoshoric acid and chloric acid.

12. The process according to claim 9, wherein the metal is used in an amount of 0.5 to 50 mol per one mol of the mixture of the cyclopentenone ester and the 4-hydroxy-2-cyclopentenone.

13. The process according to claim 9, wherein the acid is used in an amount of 1 to 30 times of the weight of the mixture of the cyclopentenone ester and the 4-hydroxy-2-cyclopentenone.

* * * * *